United States Patent [19]

Repsch

[11] Patent Number: 4,720,808

[45] Date of Patent: Jan. 19, 1988

[54] METHOD AND APPARATUS FOR MEASURING SHEET PRODUCTS

[76] Inventor: Josef Repsch, 518-401 Athabasca Avenue, Fort McMurray, Alberta, Canada, T9J 1H2

[21] Appl. No.: 734,106

[22] Filed: May 15, 1985

[51] Int. Cl.⁴ .................................. G01G 19/40
[52] U.S. Cl. ........................... 364/568; 177/1; 177/25
[58] Field of Search ............... 364/568; 177/1, 25

[56] References Cited

U.S. PATENT DOCUMENTS

| | | | |
|---|---|---|---|
| 2,822,028 | 2/1958 | Himmelheber et al. | 177/1 X |
| 3,216,515 | 11/1965 | Roberts | 177/25 |
| 3,634,187 | 1/1972 | Chari et al. | 364/568 X |
| 3,936,665 | 2/1976 | Donoghue | 364/568 X |
| 3,986,013 | 10/1976 | Brunette | 364/568 X |
| 4,038,531 | 7/1977 | Loe, Jr. | 177/25 X |
| 4,083,002 | 4/1978 | Allport | 364/568 X |

Primary Examiner—George H. Miller, Jr.
Attorney, Agent, or Firm—Fetherstonhaugh & Co.

[57] ABSTRACT

Method and apparatus for measuring the weight per unit area and providing cross-sectional, longitudinal, and diagonal profiles of density or thickness of moving manufactured sheet products. The apparatus comprises a stationary radiation source, an array of detectors, and electronic means for processing the signals from the detectors to obtain a total cross-sectional, longitudinal, and diagonal profile of density or thickness of moving manufactured sheet products. The energy output of the radiation source remains constant during a measuring operation. The apparatus utilizes a line-up of individual radiation sources delivering constant radiation. Each individual radiation source generates an equal amount of radiation. The radiation transmitted from the individual radiation source is intercepted by a detector/electronic assembly after penetrating the sheet product. The detector/electronic assembly converts the intercepted radiation to electric signals. The electric signals from the detector/electronic assembly are transmitted by conductors to electronic interface unit, signal processor and numerical display units. The invention provides an apparatus comprising the radiation source, detector/electronic assembly, electronic interface and signal processor, digital computer and numerical display modules and a method of identifying the entire transverse profile of the moving sheet products.

5 Claims, 3 Drawing Figures

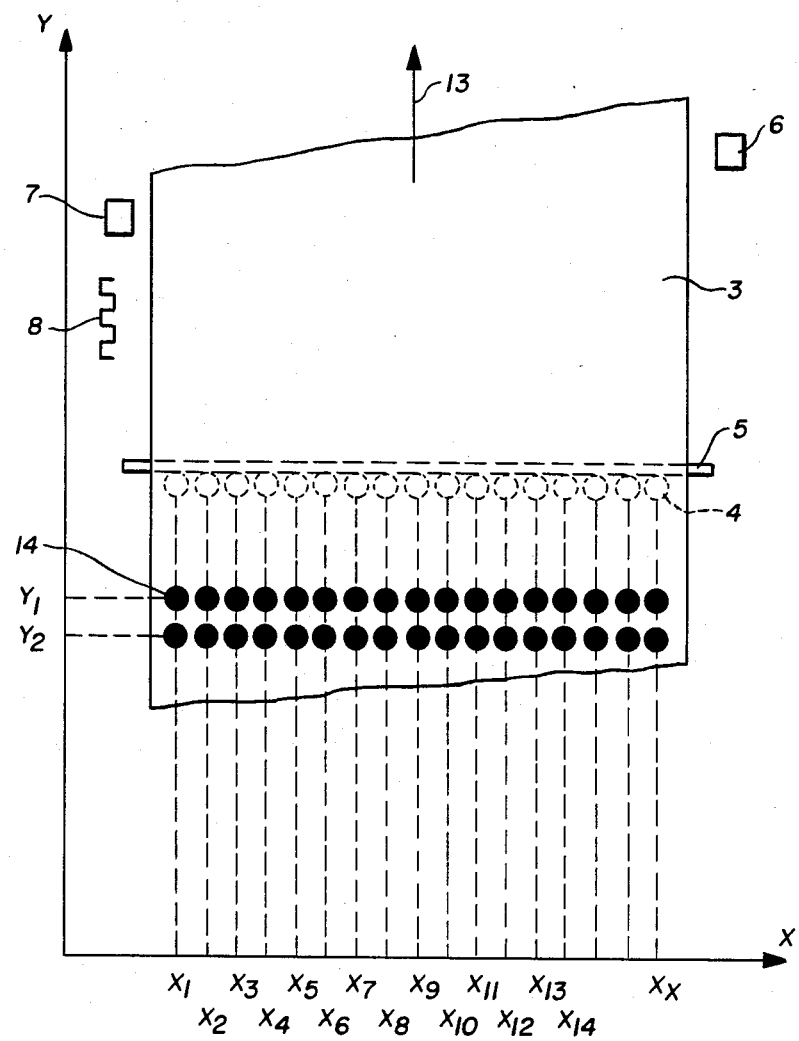

METHOD AND APPARATUS FOR MEASURING SHEET PRODUCTS

FIELD OF THE INVENTION

This invention relates to method and apparatus for performing measurements of weight per unit area, and providing cross-sectional, longitudinal, and diagonal profiles of density or thickness of moving manufactured sheet products. In particular, it relates to such measurements where the sheet products are, for example agglomerated boards made of wood chips, flakes, strands, or wood fiber; ligno-cellulosic materials; and other organic and inorganic substances.

DESCRIPTION OF THE PRIOR ART

At the present time such measurements are performed by employing scanning devices comprising a radiation source located beneath the longitudinaly moving products, and an appropriate sensing device mounted above and in precise vertical alignment with the radiation source. The movement of the scanner is such that the radiation source and the sensing device create a zig-zag measuring pattern over the longitudinally moving products.

The measurements performed by the method utilizing the zig-zag pattern provide only single spot readings of the measured variable which depicts the density or thickness at the given cross-section of the advancing products. It is thus impossible to obtain a full profile of the measured variable at a given cross-section. The method also does not provide a total readings of the longitudinal profile of the measured variable of the manufactured products.

Other measuring methods well known in this art provide only averaging of the spot readings of the measured variables within the manufactured sheet products. For this reason, these methods do not provide adequate data for reconstructing the total cross-sectional and longitudinal profiles of the measured variables.

The above methods also do not provide means for identifying the exact coordinates of the measured variables at any given point within the manufactured sheet products. They also require frequent recalibration of the measuring equipment because of varying process conditions and deterioration of the measuring devices.

SUMMARY OF THE INVENTION

This invention seeks to provide a method and an apparatus for more effective measurements of thickness and density of manufactured sheet products.

Accordingly the invention is a method of measuring the weight per unit area, density and thickness of a moving sheet by applying the techniques of penetrating radiometry the method comprising passing the sheet between a stationary linear array of detectors to take a plurality of simultaneous spot readings transverse to the direction of motion of the sheet, said stationary linear array of detectors taking readings in regular increments of time as the sheet advances longitudinally, said regular increments of time being synchronized by a sequence of pulses generated by a linear encoder and being determined by the resolution of said linear encoder, said simultaneous transverse spot readings being taken consecutively as the sheet advances to give a grid-like pattern of spot measurements covering the entire area of the advancing sheet and converting said spot measurements to electronic signals, processing those signals by a data acquisition system, interfaced with a computer adapted to generate data for the physical presentation of the results.

In a further aspect the invention is an apparatus to measure the weight per unit area, density and thickness of a moving sheet, the apparatus comprising a radiation source; a collimator for the radiation from said source; a linear array of radiation detectors spaced from said source, all said detectors being at the same distance from the source and spaced from each other; means for aligning said source, collimator and detectors in a plane; means to transmit a signal from the detectors; means to receive the signal; means to process the signal; and means to display the processed signal.

It is an object of this invention to provide a method of identifying the entire transverse profiles of the measured variable in relation to the encoded position identified by the horizontal coordinates of the consecutive detector and defined number of pulses generated by the linear encoder.

It is a further object of this invention to provide a method for identifying the entire longitudinal profile of measured variable in relation to the encoded position determined by only one of the detectors and defined number of pulses generated by the linear encoder.

It is also an object of this invention to provide a method for identifying any combination of the diagonal profiles of measured variable in relation to any encoded position determined by the horizontal coordinates of the detectors and defined number of pulses generated by the linear encoder.

It is still another object of this invention to provide a method for identifying the average value of the measured variable within the manufactured sheet products.

It is another object of this invention to provide software and hardware means allowing for display and presentation of the acquired data.

DRAWINGS

Further objects of our invention will appear from a detailed description of an embodiment. It is to be understood, however, that the present invention is in no way limited to the details of such embodiment, but is capable of numerous modifications within the scope of the appended claims.

FIG. 3 shows the concept of identifying the coordinates of the measured variables.

DESCRIPTION OF THE PREFERRED EMBODIMENTS

Figure 1:
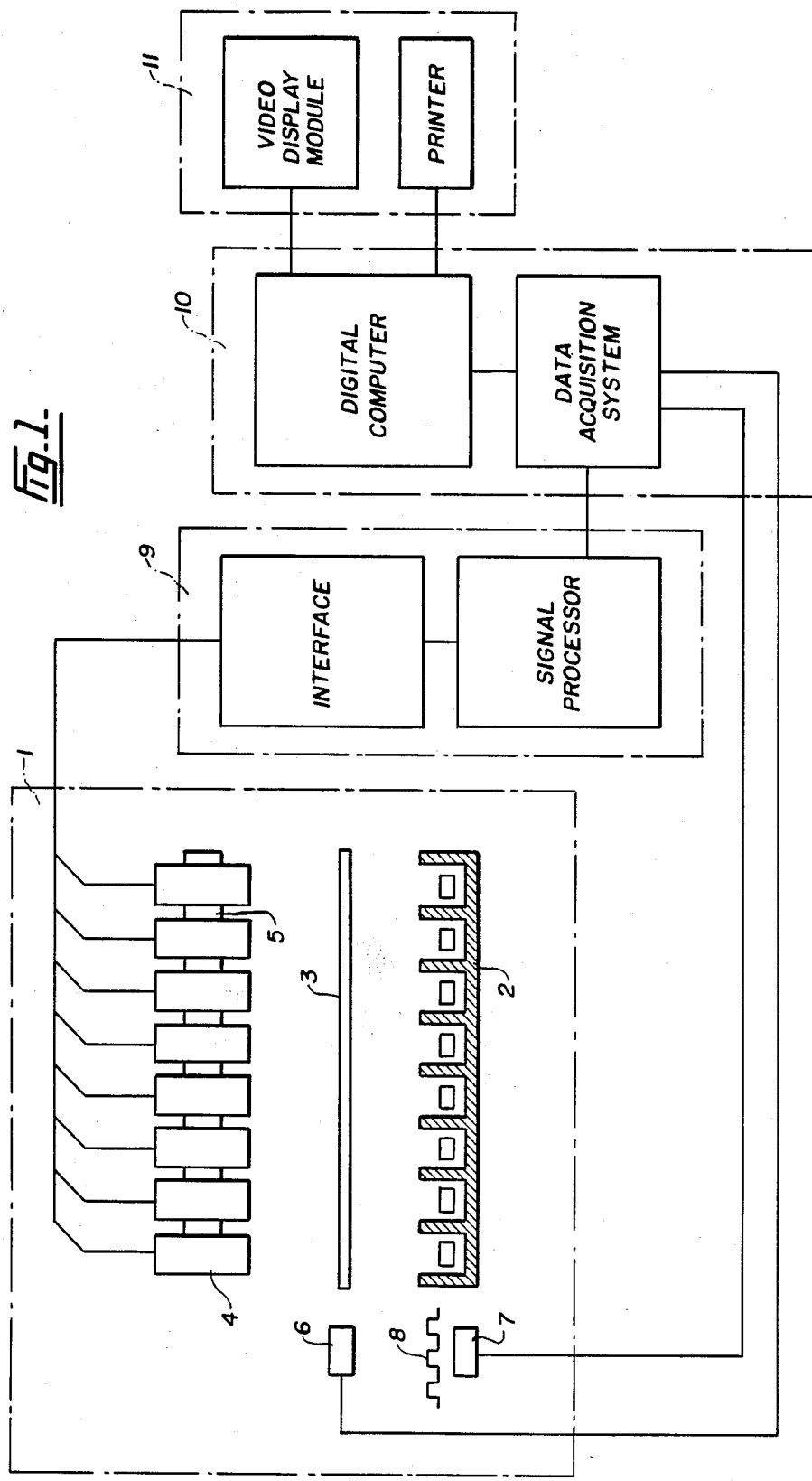
FIG. 1 is a block diagram of the apparatus embodying the invention.

A preferred embodiment of the novel apparatus for measuring of weight per unit of manufactured sheet products is shown diagrammatically in FIG. 1.

All mechanical, electrical, and electronic components of the apparatus are well known in the industry and need not be described in detail.

The detector/electronic assembly, interface and power supply module, and signal processor and display unit, depicted on FIG. 1 as items 4 and 7 are disclosed in the patent application filed by R. A. Tawil, A. Scalanczy, K. Velbeck, J. Chamberlain, D. Leslie, and C.

W. King; all of Harshaw/Filtrol Partnershp, of Solon, Ohio.

At the time of filing this patent, any reference numbers related to the patent application of Harshaw/Filtrol were not available. It is known to us that the patent of Harshaw/Filtrol was filed with the U.S. Patent Office.

Figure 2:
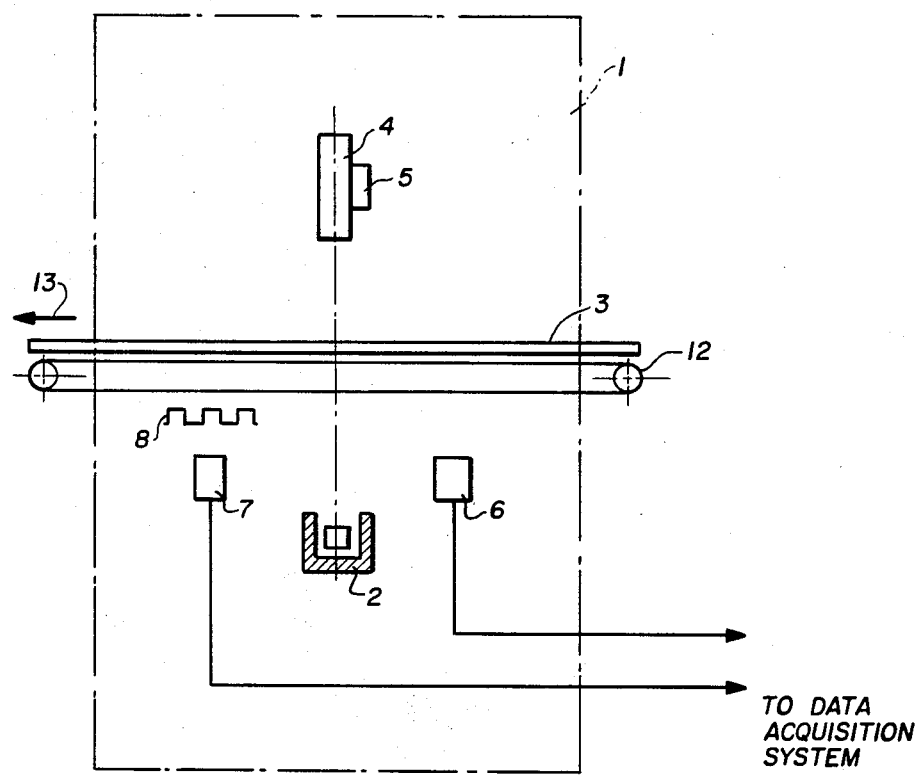
FIG. 2 is a diagrammatic side view of the longitudinally advancing products and the stationary measuring assembly.

The sheet products 3 are carried over the array of detectors by transporting devices comprising sets of rolls, endless belts, or other conveying means 12 in FIG. 2. The conveying means for transporting sheet products are mounted on a supporting frame which is not shown and is not a part of this invention.

All components of the measuring assembly are disposed on the frame 1, shown symbolically.

The radiation source 2, located beneath the advancing sheet product, comprises a line of individual compartments each containing a radiation substance. Each individual compartment is in precise vertical and horizontal alignment with the detector/electronic assembly.

The radiation substance used in this invention may be any type of radiation source emitting Gamma or Beta rays, X-rays or neutrons.

The individual detectors 4 are disposed on the base 5 in such a way that their displacement allows for reception of the full amount of the emitted radiation from the radiation source 2 and conversion of the received radiation into readable electrical signals as it is shown in FIG. 1.

The cross-sections of the radiation source 2 and detectors 4 are disposed within the same plane.

The detectors 4 provide discrete coding of the coordinates $x_1$ to $x_n$ across the manufactured sheet products as shown in FIG. 3.

A linear encoder 7, a device well known in the industry, is disposed on the frame 1 of the measuring assembly to provide a sequence of pulses 8 encoding the longitudinal movement 13 of the manufactured sheet products as shown in FIG. 3.

Transverse, discrete encoding of the advancing sheet products 3 by the detectors 4, together with the longitudinal encoder of the movement of the sheet products by the sequence of the pulses 8 create a grid-like pattern of spot measurements over the advancing sheet products 3 as shown in FIG. 3.

The base 5 must be of such a shape that allows for the installation of detectors 4 at an equal distance from the radiation source 2.

The proximity switch 6 is a device well known in the industry and is disposed on the frame 1 of the measuring assembly. The proximity switch 6 generates an electrical imipulse when it detects the presence of the advancing sheet products.

The assemblies 9, 10, and 11 as they are shown in FIG. 1, comprise electronic components well known in the industry for the acquisition, processing, and display of electric and electronic signals received from the detectors 4.

The linear encoder 7, proximity switch 6, and detectors 4 are connected by appropriate means allowing for the transmission of electrical and electronic signals over the distance between the above devices and the data acquisition system. The data acquisition system is an integral part of the electronic data processing assembly as shown in FIG. 1.

It is well known that the measurements of the weight per unit area can be performed by penetrating radiometry techniques based on the following equation:

$$I = I_0 e^{-\mu x} \quad (1)$$

where I is the transmitted intensity of the radiation, $I_0$ is the intensity of the incident radiation, e is the natural log base, $\mu$ equals the linear attenuation coefficient, and x is the weight per unit area of the measured material. The equation (1) may be presented in the following form:

$$x = \frac{1}{\mu} \ln \frac{I_0}{I} \quad (2)$$

The weight per unit area x as described by the equation (2) may be defined also as a product of the density, expressed as weight per unit volume, and thickness, expressed as units of length, as:

$$x = d \cdot t \quad (3)$$

where x is the weight per unit area, d is the density of the product, and t is the thickness of the product.

The apparatus is calibrated in terms of "weight per unit area" and if the product density is maintained constant, the results of the measurements are presented as thickness of the measured product.

Conversely, if the thickness of the product is maintained constant, the results of the measurements are expressed as the density of the measured product.

The calibration techniques to be applied for calibrating the apparatus are well known in the industry and need not be described.

From the above it will be readily understood that the apparatus described will attain the objects of the invention.

I claim:

1. A method of measuring the weight per unit area, density and thickness of a moving sheet by applying the techniques of penetrating radiometry the method comprising:

passing the sheet between a stationary linear array of detectors to take a plurality of simultaneous spot readings transverse to the direction of motion of the sheet, said stationary linear array of detectors taking readings in regular increments of time as the sheet advances longitudinally, said regular increments of time being synchronized by a sequence of pulses generated by a linear encoder and being determined by the resolution of said linear encoder, said simultaneous transverse spot readings being taken consecutively as the sheet advances to give a grid-like pattern of spot measurements covering the entire area of the advancing sheet and converting said spot measurements to electronic signals, processing those signals by a data acquisition system, interfaced with a computer adapted to generate data for the physical presentation of the results and presenting the selected measured values of density and thickness in the form of a contour map.

2. Method as claimed in claim 1 in which progressive deterioration and the rate of progressive deterioration of a measured value of the sheet is displayed.

3. Apparatus to measure the weight per unit area, density and thickness of a moving sheet, the apparatus comprising a radiation source;

a collimator for the radiation from said source;
   a linear array of radiation detectors spaced from said source, all said detectors being at the same distance from the source, spaced from each other and disposed to receive the full amount of the emitted radiation and convert the received radiation into recognizable electrical signals with the detector to take continuous readings of the incident radiation for the purpose of calibration;

means for aligning said source, collimator and detectors in a plane;

means to transmit a signal from the detectors;

means to receive the signal;

means to process the signal; and means to display the processed signal.

4. A method of measuring the weight per unit area, density and thickness of a moving sheet by applying the techniques of penetrating radiometry the method comprising:

passing the sheet between a stationary linear array of detectors to take a plurality of simultaneous spot readings transverse to the direction of motion of the sheet, said stationary linear array of detectors taking readings in regular increments of time as the sheet advances longitudinally, said regular increments of time being synchronized by a sequence of pulses generated by a linear encoder and being determined by the resolution of said linear encoder, said simultaneous transverse spot readings being taken consecutively as the sheet advances to give a grid-like pattern of spot measurements covering the entire area of the advancing sheet and converting said spot measurements to electronic signals, processing those signals by a data acquisition system, interfaced with a computer adapted to generate data for the physical presentation of the results and presenting the selected measured values of density or thickness of the percentage of the total area of the manufactured sheet products.

5. Method as claimed in claim 4 in which the total average of density or thickness of the manufactured sheet products is presented.

* * * * *